US00PP10430P

United States Patent [19]

Kientzler

[11] Patent Number: Plant 10,430

[45] Date of Patent: Jun. 2, 1998

[54] NEW GUINEA IMPATIENS PLANT NAMED '214'

[75] Inventor: Ludwig Kientzler, Gensingen, Germany

[73] Assignee: Paul Ecke Ranch, Inc., Encinitas, Calif.

[21] Appl. No.: 797,128

[22] Filed: Feb. 10, 1997

[51] Int. Cl.[6] ..... A01H 5/00

[52] U.S. Cl. ..... Plt./87.6

[58] Field of Search ..... Plt./87.6

*Primary Examiner*—James R. Feyrer
*Attorney, Agent, or Firm*—C. A. Whealy

[57] ABSTRACT

A new and distinct cultivar of New Guinea Impatiens plant named '214', characterized by its medium pink-colored flowers; freely flowering habit; outwardly spreading, rounded and mounding growth habit; freely branching plant habit; and dark green, matte, non-variegated foliage.

2 Drawing Sheets

The present invention relates to a new and distinct cultivar of New Guinea Impatiens plant, botanically known as *Impatiens hawkeri*, and hereinafter referred to by the cultivar name '214'.

The new cultivar is a product of a planned breeding program conducted by the inventor in Gensingen, Germany. The objective of the breeding program was to develop new varieties that have a uniform plant habit, attractive flower colors, good flower form and numerous flowers per plant.

The new cultivar originated from a cross made by the inventor of a proprietary seedling selection identified as Q672 as the male, or pollen parent, with the proprietary seedling selection identified as I212 as the female, or seed patent. The cultivar '214' was discovered and selected by the inventor as a flowering plant within the progeny of the stated cross in a controlled environment in Gensingen, Germany. Asexual reproduction of the new cultivar by terminal cuttings taken at Gensingen, Germany, has shown that the unique features of this new Impatiens are stable and reproduced true to type in successive generations of asexual reproduction.

The following traits have been repeatedly observed and are determined to be the unique characteristics of '214'. These characteristics in combination distinguish '214' as a new and distinct cultivar:

1. Medium pink-colored flowers.
2. Freely flowering.
3. Outwardly spreading, rounded and mounding growth habit.
4. Freely branching plant habit.
5. Dark green, matte, non-variegated foliage.

The new New Guinea Impatiens is similar in flower color to the New Guinea Impatiens cultivar 'BFP-397 Light Salmon' (disclosed in U.S. Plant Pat. No. 9,213). However in side-by-side comparisons in Encinitas, Calif. under commercial practice, plants of the new New Guinea Impatiens differed from plants of the cultivar 'BFP-397 Light Salmon' in the following characteristics:

1. Plants of the new New Guinea Impatiens more outwardly spreading than plants of the cultivar 'BFP-397 Light Salmon'.

2. Plants of the new New Guinea Impatiens are more freely branching than plants of the cultivar 'BFP-397 Light Salmon'.

3. Leaves of plants of the new New Guinea Impatiens are solid green in color whereas leaves of plants of the cultivar 'BFP-397 Light Salmon' are variegated in color. In addition, the color of the lower leaf surfaces of plants of the new New Guinea Impatiens is dark red whereas the color of the lower leaf surfaces of plants of the cultivar 'BFP-397 Light Salmon' is green.

4. Flowers of plants of the new New Guinea Impatiens are slightly smaller and less rounded than flowers of plants of the cultivar 'BFP-397 Light Salmon'.

5. Flowers of plants of the new New Guinea Impatiens have a tri-color appearance whereas flowers of plants of the cultivar 'BFP-397 Light Salmon' have a bi-color appearance.

6. Flower color of plants of the new New Guinea Impatiens does not fade compared to plants of the cultivar 'BFP-397 Light Salmon'.

7. Flower peduncles of the new New Guinea Impatiens are longer but not as upright as flower peduncles of plants of the cultivar 'BFP-397 Light Salmon'.

A detailed comparison of plants of the new New Guinea Impatiens and the cultivar 'BFP-397 Light Salmon' appears in Chart A at the end of the specification.

The accompanying colored photographs illustrate the overall appearance of the new cultivar, showing the colors as true as it is reasonably possible to obtain in colored reproductions of this type.

The first photograph comprises a top perspective view of a typical plant of '214'. The second photograph comprises a close-up view of typical flowers and upper (left) and lower (right) surfaces of leaves of the cultivars 'BFP-397 Light Salmon' (top of photo) and '214' (bottom of photo).

The flower and foliage colors in the photographs may differ from the actual colors due to light reflectance.

The cultivar '214' has not been observed under all possible environmental conditions. The phenotype may vary somewhat with variations in environment such as temperature and light intensity, without, however, any variance in genotype. The following observations, measurements and comparisons describe plants grown 25-cm hanging baskets in Encinitas, Calif., under commercial practice in a fiberglass-covered greenhouse with day temperatures ranging from 23 to 29C. and night temperatures ranging from 16 to 18C and light levels averaging 3,000 footcandles.

In the following description, color references are made to The Royal Horticultural Society Colour Chart except where general terms of ordinary dictionary significance are used.

Classification:

*Botanical.*—*Impatiens hawkeri* '214'.

*Commercial.*—New Guinea Impatiens cv. '214'.

Parentage:

*Male parent.*—Proprietary seedling selection Q672.

*Female parent.*—Proprietary seedling selection I212.

Propagation:

*Type cutting.*—Terminal cuttings.

*Time to initiate roots.*—About 15 days with 21C. soil temperature.

Plant description:

*Plant form.*—Outwardly spreading, rounded and mounding.

*Growth habit.*—Vigorous. Freely branching, dense and bushy. Suitable for 10 to 25-cm containers.

*Plant size.*—Height: About 32 cm. Width or spread: About 58 cm.

*Lateral branches.*—Quantity: About eight. Size: Length: 17 to 20 cm. Diameter: 1.6 to 1.7 cm. Internode length: 7.5 to 8 cm. Color: Darker than 57A.

*Foliage description.*—Leaves simple, generally symmetrical, abundant, opposite or in whorls of three, horizontal to plant and flat in aspect. Size, largest leaves: Length: 10 to 13 cm. Width: About 5.5 cm. Shape: Ovate with acuminate apex, attenuate base and ciliate margin. Texture: Smooth, matte. Color: Young foliage, upper surface: 147A. Young foliage, lower surface: 59A. Fully expanded foliage, upper surface: Darker than 139A. Fully expanded foliage, lower surface: 59A. Venation, upper surface: 59B. Venation, lower surface: 59A. Petiole: Size: Length: About 4 cm. Diameter: About 5 mm. Color: 59A.

Flower description:

*Flower type and habit.*—Medium pink flowers. Freely and continuously flowering. Flowers arise from leaf axils. Usually seven to nine flowers per lateral branch. Flowers positioned above the foliage and face outward. Flowers flat and rounded to rectangular. Flowers persistent.

*Flowering season.*—Year-round under greenhouse conditions. In the garden, flowering is continuous from spring until fall.

*Flower size.*—Length: About 6.5 cm. Width: About 6 cm. Depth: About 5 mm.

*Flower buds.*—Size: Length: About 2.5 cm. Diameter: About 1.5 cm. Shape: Ovoid. Color: 52A/52B.

*Petals.*—Quantity: Five. Size (largest petals): Length: Top petal: About 3 cm. Middle petals: About 3.4 cm. Bottom petals: About 4 cm. Width: Top petal: About 5 cm. Middle petals: About 3.5 cm. Bottom petals: About 4.5 cm. Shape: Cordate with emarginate apex, cuneate or obtuse base and entire margin. Texture: Velvety, smooth. Color: When opening, upper surface: Iridescent, 50A. When opening, lower surface: Iridescent, 52B/52C. Fully opened, upper surface: Iridescent, 50B at margins with 52C at center grading to white with magenta, 57A/57B, at base. Fully opened, lower surface: Iridescent, 52B/52C. Fading to: 52C.

*Spur.*—Length: About 5 cm. Shape: Narrow and curved. Color: Mostly 60B, 59A at tip.

*Peduncles.*—Length: About 5 cm. Angle: Mostly outward. Strength: Strong. Color: 60A/60B.

*Reproductive organs.*—Androecium: Stamen number: Five, anthers fused, filaments free. Anther shape: Obovate. Anther size: 5 by 4 mm. Anther color: Pinkish cream. Amount of pollen: Moderate. Pollen color: Cream. Gynoecium: Five-loculate fused. Gynoecium length: About 6 mm. Gynoecium color: Darker than 59A.

Disease resistance: Under commercial conditions, resistance nor susceptibility to pathogens has not been observed.

Seed development: Seed production is not usually observed.

CHART A

| CHARACTERISTIC | '214' | 'BFP-397 LIGHT SALMON' |
|---|---|---|
| GROWTH HABIT | Upright and outwardly spreading, mounding | Mostly upright with open habit |
| NUMBER OF LATERAL BRANCHES PER PLANT | About 8 | 5 to 6 |
| STEM COLOR | Darker than 57A | 148B with flecks of 60C |
| LEAF COLOR, YOUNG, UPPER SURFACE | 147A | 147A |
| LEAF COLOR, YOUNG, LOWER SURFACE | 59A | 146B |
| LEAF COLOR, MATURE, UPPER SURFACE | Darker than 139A | 147A with yellow green, 151A/151B, variegation |
| LEAF COLOR, MATURE, LOWER SURFACE | 59A | 146B to 144A/144B |
| LEAF VENATION COLOR, UPPER SURFACE | 59B | 36A |
| LEAF VENATION COLOR, LOWER COLOR | 59A | 147B/147C |
| PETIOLE COLOR | 59A | 63B/63C |
| FLOWER LENGTH | About 6.5 cm | About 7 cm |
| FLOWER WIDTH | About 6 cm | About 7 cm |
| SPUR COLOR | 60B with 59A at tip | 59A with 144A at tip |
| PETAL COLOR, WHEN OPENING, UPPER SURFACE | 50A | More orange than 43C |
| PETAL COLOR, WHEN OPENING, LOWER SURFACE | 52B/52C | 50B |
| PETAL COLOR, OPENED, UPPER SURFACE | 50B at margins with 52C at center grading to white with magenta, 57A/57B, at base. | 43C with 43D towards center grading to white with 63B at base |
| PETAL COLOR, OPENED, LOWER SURFACE | 52B/52C | 43D |
| PETAL COLOR, FADING TO | 52C | 43D to white |
| PENDUNCLE LENGTH | About 5 cm | 4 to 4.2 cm |
| PEDUNCLE ANGLE | Outward | Upright |
| PEDUNCLE COLOR | 60A/60B | 50A |
| GYNOECIUM COLOR | Darker than 59A | 137B |

It is claimed:

1. A new and distinct cultivar of New Guinea Impatiens plant named '214', as illustrated and described.

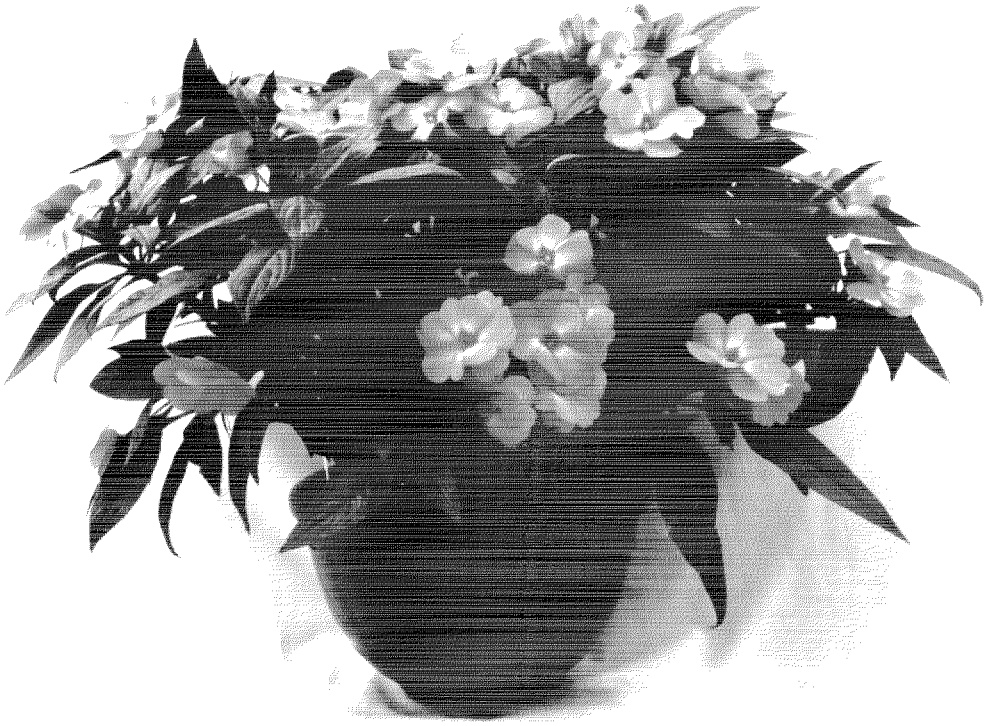

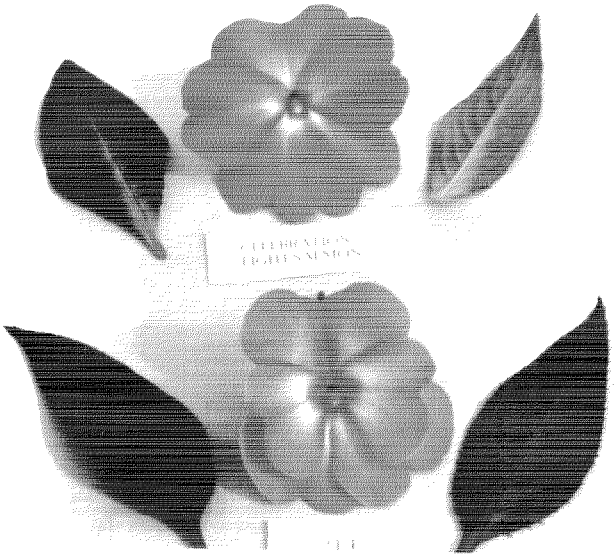

* * * * *